United States Patent [19]
Gueguen et al.

[11] Patent Number: 4,611,086
[45] Date of Patent: Sep. 9, 1986

[54] PROCESS FOR HYDRATION OF OLEFINS

[75] Inventors: Claude Gueguen, Septeme Pont L'Eveque; François Figueras, Montpellier; François Fajula, Theyran, all of France

[73] Assignee: Elf France, Paris, France

[21] Appl. No.: 606,641

[22] Filed: May 3, 1984

[30] Foreign Application Priority Data

May 6, 1983 [FR] France ............................ 83 07649

[51] Int. Cl.⁴ .................... C07C 29/04; C07C 31/12; C07C 31/125
[52] U.S. Cl. .................................................. 568/897
[58] Field of Search ........................................ 568/897

[56] References Cited

U.S. PATENT DOCUMENTS 4,214,107 7/1980 Chang et al. ...................... 568/897
4,528,410 7/1985 Sakamoto et al. ................. 568/897

Primary Examiner—J. E. Evans
Attorney, Agent, or Firm—Burgess, Ryan & Wayne

[57] ABSTRACT

A process for the preparation of aliphatic alcohols by hydration of olefins in the presence of a catalyst comprising a zeolitic crystalline silicoaluminate of the offretite type. The offretite used can be natural or sythetic. Particularly convenient among the olefins are olefins of low molecular weight having up to 5 carbon atoms. The alcohols obtained are used as solvents, as bases for lubricants and as adjuvants of essences.

12 Claims, No Drawings

PROCESS FOR HYDRATION OF OLEFINS

The invention is a process for preparation of aliphatic alcohols by hydration of olefins. The alcohols obtained are useful as solvents, as bases for lubricants and as adjuvants of essences.

BACKGROUND OF THE INVENTION

The preparation of alcohols by hydration of olefins in acid medium is well known. Thus, isopropyl alcohol is obtained by hydration of propylene in a sulfuric acid medium. However, the use of sulfuric acid results in corrosion problems and reconcentration of the acid requires a large consumption of energy.

An improvement in the process consists in the utilization of solid acid catalysts such as phosphoric acid deposited on silica or clay. This type of catalyst is described in U.S. Pat. No. 4,299,730. The high temperature needed for the reaction has an unfavorable effect on the yield and selectivity which has prevented the commercial development of this process.

The use of catalysts of the zeolite type has also been considered. According to French Pat. No. 2,281,344, zeolite Y containing chromium cations and rare earths can be used as the catalyst. The cations however, impart certain acidity to the catalyst.

Other processes use the zeolite catalysts in a protonated (acid) form. Thus, U.S. Pat. No. 4,214,107 recommends the use of a synthetic zeolite called ZSM-5 in an acid form.

Japanese Pat. No. 7,245,323 describes the use of mordenite and faujasite catalysts in an acid form.

However, these zeolites are not very active catalysts and do not provide high conversions. Olefins that are not very reactive such as the n-butenes do not react in the presence of said zeolites.

BRIEF SUMMARY OF THE INVENTION

According to the present invention, aliphatic alcohols are prepared by hydration of the corresponding olefin at a temperature of from about 100° to 400° C., a pressure of from about 20 to 100 bars, a liquid spatial velocity (VVH) of from about 0.2 to 5 m$^3$/m$^3$/h, a molar ratio water/olefin being between about 1:1 and 8:1, in the presence of a catalyst comprising a zeolitic crystalline silicoaluminate of the offretite type. The offretite used may be either natural offretite or a synthetic offretite having the crystalline structure of natural offretite and a molar ratio silica/alumina between about 2:1 and 50:1.

DETAILED DESCRIPTION OF THE INVENTION

Natural offretite has been described by J. M. Bennett and J. A. Gard (Nature 214 1005 (1967)). It contains no crystalline defects and is clearly distinguished from erionite and zeolite T.

The structure of the offretite useful in the present invention comprises a combination of cylindrical, rectilinear and parallel channels having an opening diameter of approximately 0.63 nm. These channels are delimited by clusters by hexagonal prisms and by frames of small dimensions.

The clusters proper are bound by frameworks having on eight sides apertures accessible to molecules and have a critical diameter of about 0.5 nm.

The offretite belongs to group 2 of the universally accepted classification of MEIER (W. M. MEIER Molecular Sieves, Society of Chemical Industry, London 1968), and the X-ray diffraction spectrum has the significant peaks given in Table I that follows:

TABLE 1

| khl | d(A) | I$_r$ | hkl | d(A) | I$_r$ | hkl | (A) | I$_r$ |
|---|---|---|---|---|---|---|---|---|
| 100 | 11.50 | 100 | 310 | 3.190 | 17 | 311 | 2.126 | 4 |
| 100 | 6.64 | 20 | 311 | 2.942 | 3 | 303 | 2.110 | 2 |
| 200 | 5.76 | 35 | 400 | 2.880 | 64 | 421 | 2.091 | 2 |
| 201 | 4.581 | 4 | 212 | 2.858 | 15 | 510 | 2.068 | 2 |
| 210 | 4.352 | 59 | 401 | 2.693 | 3 | 511 | 1.995 | 2 |
| 300 | 3.837 | 43 | 320 | 2.642 | 4 | 502 | 1.967 | 2 |
| 211 | 3.774 | 11 | 410 | 2.510 | 20 | 430 | 1.893 | 1 |
| 102 | 3.600 | 3 | 500 | 2.300 | 5 | 520 | 1.844 | 3 |
| 220 | 3.322 | 22 | 420 | 2.177 | 2 | | | |

I$_R$ (relative intensity): I/I$_O$ × 100

This zeolite develops a higher acidity than zeolite Y. Because of the higher acidity and the accessibility of its channels, it is a very effective catalyst.

The elementary composition of the natural offretite is represented by the formula:

$(M_1 M_2 \ldots)_2 Al_{14} Si_{14} O_{36} 14 H_2 O$.

Synthesis of the zeolite makes it possible to modify the silica and alumina content.

The zeolites useful in the present invention are prepared by crystallizing the composition at a temperature between about 0° and 300° C., from a supersaturated alkaline solution of alumina and silica gels recently precipitated. According to U.S. Pat. No. 3,947,482 to Grace, the crystalline network is formed around an organic nucleation agent, generally a quaternary ammonium composition.

U.S. Pat. No. 4,093,699 to Zeochem Corporation describes a synthesis without use of a nucleation agent. In this process, the molar ratios of the components and operating parameters are well defined and must be strictly observed.

The synthetic offretites according to the invention are defined by the formula:

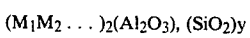

$(M_1 M_2 \ldots)_2 (Al_2 O_3), (SiO_2)y$ where y is between 2 and 50, preferably between 5 and 15, M$_1$ and M$_2$ are selected from cations of Groups I and II of the periodic classification.

The original cations of the zeolite can be exchanged at a 70% level with a solution of ammonium acetate according to well-known methods. The catalyst obtained is calcined in air at 500° C. for 5 hours or more. The original cations can likewise be replaced by a proton, by metallic ions such as potassium and chromium, and also by mixtures of cations. The exchange methods generally applied are those described in the work "Zeolite Chemistry and Catalysis" by J. A. Rabo, A.C.S. Monograph 111 (Washington, 1977).

The catalyst useful in the present invention can comprise offretite and an active or inert material such as an argile, alumina, or a binary silica-alumina, silica-magnesia composition.

Particularly useful in the practice of the present invention are olefins of low molecular weight having up to 5 carbon atoms such as ethylene, propylene, n-butene-1, cis- and trans-n-butene-2, isobutene, butadiene and pentenes. It is also possible to use fractions containing a mixture of said olefins, as for example, fraction C$_4$, a mixture of butane, butenes and butadiene, or fraction C5, a mixture of methyl butanes and n-pentenes.

The straight-chain olefins such as the n-pentenes, n-butenes and propylene are normally not very reactive and their hydration is very difficult. The active catalysts of the invention permit the hydration of n-pentenes and n-butenes alone or mixed with isopentenes, isobutene and propylene.

The hydrocarbon feed is mixed, prior to entering the reactor, with water vapor. The molar ratio of water to olefin is preferably from about 1:1 to 8:1.

The reaction temperature is suitably from about 100° to 400° C. The temperature selected depends on the reactivity of the olefin. A study of the thermodynamic equilibrium shows that the formation of alcohol is favored at low temperature. Therefore, the process is generally carried out at the lowest temperature compatible with a desired level of conversion.

The pressure is generally in the range of from about 20 to 100 bars total pressure. The liquid spatial velocity of the feed or VVH is suitably between about 0.2 and 5 m3/m3/h. The process is illustrated by the non-limiting examples given below.

EXAMPLES

Table II summarizes the characteristics of the offretite silicoaluminate catalysts used in the examples.

The cation exchanges were made on 1 gram of zeolite in 500 cm3 water. The zeolite was contacted with an aqueous solution containing a calculated concentration of metallic salt. The exchange took place while stirring at room temperature. The catalyst was then filtered, washed with distilled water, dried at 100° C. for 12 hours, ground and activated. The catalyst was activated in a thin bed by calcining under a flow of dry air.

EXAMPLE 1

Table 3 summarized the results of the hydration of isobutene in t-butanol in the presence of different offretites. Catalysts 2 and 3 have an identical formula, but form part of two different production batches. The results demonstrate the good reproducibility of the process.

EXAMPLE 2

Table 4 summarizes the results on the hydration of n-butenes and isobutene. The n-butenes are principally 2-butene in the cis and transforms.

EXAMPLE 3

Table 5 summarizes the effect of the parameters on the hydration of n-butenes. The conversion of n-butenes requires a higher temperature and pressure than that required for an equivalent conversion of isobutene.

EXAMPLES 4 AND 5

Tables 6 and 7 summarize the results of the hydration of n-butenes, n-pentenes and isopentenes.

TABLE 2

| | | CATALYSTS | |
|---|---|---|---|
| No. | Name | Si/Al atom ratio | Rate of exchange of the initial cations (%) |
| 1 | offretite KH | 3.7 | 66 |
| 2 | offretite KH Cr | 3.7 | 70 |
| 3 | offretite KG Cr | 3.7 | 70 |
| 4 | offretite KH Ce | 3.7 | 70 |
| 5 | offretite K Cr | 3.7 | 72 |
| 6 | offretite KH | 8.5 | 70 |
| 7 | offretite KH Cr | 3 | 80 |
| 8 | offretite KH | 3 | 70 |
| 9 | offretite KH | 3.9 | 70 |
| 10 | offretite KH | 3 | 70 |
| 11 | offretite KH | 3 | 66 |
| 12 | Δ Cat. II de-aluminized | 3.8 | 83 |
| 13 | Δ Cat. II de-aluminized and calcined at 500° C. | 4.96 | 86 |

K = potassium
Cr = chromium
Ce = cerium
Δ The catalyst was dealuminized by a method in "Zeolite Catalyst and Chemistry", J.A., RABO, ACS Monograph 111 (Washington, 1977)

TABLE 3

REACTIONS OF ISOBUTENE AT 200° C.

| Catalyst Name No | Temperature °C. | H2O/isobutene mole/mole | Pressure bar | Conversion to t-butanol molar % | Yield* of t-butanol |
|---|---|---|---|---|---|
| 2 KH Cr offretite | 200 | 5 | 41 | 9.05 | 19.4 |
| 3 KH Cr offretite | 200 | 5 | 41 | 9 | 19.2 |
| 5 K Cr offretite | 200 | 4.4 | 45 | 4.7 | 10 |
| 7 KH Cr offretite | 200 | 5 | 45 | 9 | 19.6 |

TABLE 4

REACTIONS OF THE MIXTURE OF n-BUTENES-ISOBUTENE AT 200° C. ON OFFRETITE

| Catalyst Name No. | Temperature °C. | Pressure bar | H2O/olefine mole/mole | n-butene/ isobutene mole/mole | % molar conversion isobutene/ n-butene | | Yield* of corres. alcohol | |
|---|---|---|---|---|---|---|---|---|
| | | | | | iso-butene | n-butene | iso-butene | n-butene |
| 2 KH Cr offretite | 200 | 45 | 4.4 | 3 | 6.7 | 0.2 | 3.6 | 0.4 |

*yield is expressed as thousands of gram mols per gram per hour

TABLE 5

EFFECT OF THE EXPERIMENTAL PARAMETERS ON THE HYDRATION OF n-BUTENES

| Catalyst Name No | Temperature °C. | H$_2$O/butene mole/mole | Pressure bar | % molar conversion | Yield* |
|---|---|---|---|---|---|
| 1 KH offretite | 200 | 44 | 45 | traces | |
| 1 KH offretite | 200 | 6 | 46 | traces | |
| 1 KH offretite | 250 | 4.4 | 65 | 0.9 | 1.9 |

TABLE 6

HYDRATION OF n-BUTENE ON OFFRETITE KH - EFFECT OF THE OFFRETITE STRUCTURE

| Catalyst Name No | Temperature °C. | H$_2$O/n-butene mole/mole | Pressure bar | Yield expressed in % of thermodynamic equilibrium | Yield* of butanol |
|---|---|---|---|---|---|
| 1 offretite KH | 250 | 4.5 | 65 | 28 | 2.63 |
| 8 offretite KH | 250 | 4.5 | 65 | 20 | 1.88 |
| 9 offretite KH | 250 | 4.5 | 65 | 33 | 3.1 |
| 10 offretite KH | 250 | 4.5 | 65 | 16 | 1.5 |
| 11 offretite KH | 250 | 4.5 | 65 | 19 | 1.85 |
| 12 offretite | 250 | 4.5 | 65 | 40 | 3.7 |
| 13 offretite | 250 | 4.5 | 65 | 64 | 6.02 |

TABLE 7

EFFECT OF THE EXPERIMENTAL PARAMETERS ON THE HYDRATION OF n-PENTENES AND ISOPENTENES

| Catalyst Name No | Olefin | Temperature °C. | H$_2$O/pentene mole/mole | Pressure bar | % Molar conversion | Yield expressed in % of thermodynamic equilibrium | Yield* in alcohol |
|---|---|---|---|---|---|---|---|
| 8 offretite KH | 2-methyl-2-pentene | 200 | 4.5 | 35 | 4.46 | 80 | 8.42$^a$ |
| 8 offretite KH | 2-methyl-2-pentene | 250 | 4.5 | 67.5 | 4.42 | 85 | 8.36$^a$ |
| 8 offretite KH | 2-pentene | 250 | 4.5 | 65 | traces | — | — |
| 8 offretite KH | 2-pentene | 300 | 4.5 | 115 | 3.8 | 90 | 7.04$^b$ |

$^a$2-methyl-2-pentanol
$^b$2-pentanol and 3-pentanol
*yield is expressed as thousands of gram mols per gram per hour.

What is claimed:

1. A process for the preparation of an aliphatic alcohol which comprises: hydrating an olefin at a temperature of from about 100° to 400° C. and a pressure of from about 20 to 100 bars, at a liquid spatial velocity of the feed (VVH) of from about 0.2 to 5 m3/m3/h at a molar ratio water/olefin between about 1:1 and 8:1, in the present of a catalyst comprising dealuminized offretite zeolitic crystalline silicoaluminate.

2. A process according to claim 1, wherein the zeolite is a natural offretite.

3. A process according to claim 1, wherein the zeolite is a synthetic offretite having the crystalline structure of natural offretite and a chemical formula (M$_1$M$_2$ . . . )$_2$(Al$_2$O$_3$)(SiO$_2$)y wherein y is between 2 and 50 and M$_1$ and M$_2$ are selected from Groups I and II of the Periodic Table.

4. A process according to claim 1, wherein the original cations of the offretite are at least partially exchanged with at least one ion selected from the group consisting of metal ions, ammonium ions and hydrogen ions.

5. A process according to claim 1, 2, 3 or 4 wherein sodium and potassium ions of the offretite are exchanged at 70% with an ammonium acetate solution and the catalyst thus obtained is treated for at least about 5 hours at about 500° C. in the presence of air prior to being used in the reaction.

6. A process according to claim 1, 2, 3 or 4 wherein the potassium and sodium ions of the offretite are exchanged with chromium ions.

7. A process according to claim 1 or 3, wherein the molar ratio of silica/alumina in the offretite is between about 5 and 15.

8. A process according to claims 1, 2, 3, or 4 wherein the olefin has from 2 to 5 carbon atoms.

9. A process according to claim 1, 2, 3 or 4 wherein the olefin comprises a petroleum fraction comprising saturated and unsaturated hydrocarbons having four carbon atoms.

10. A process according to claim 9, wherein the olefin comprises n-butenes.

11. A process according to claim 1, 2, 3 or 4 wherein the olefin comprises a petroleum fraction comprising saturated and unsaturated hydrocarbons having five carbon atoms.

12. A process according to claim 11, wherein the olefin comprises n-pentenes.